United States Patent [19]

Ingle et al.

[11] Patent Number: 5,104,391
[45] Date of Patent: Apr. 14, 1992

[54] OPTICAL FIBER BREAKAGE DETECTION SYSTEM

[75] Inventors: Frank W. Ingle, Palo Alto; Michael Aita, Sunnyvale, both of Calif.

[73] Assignee: Advanced Cardiovascular Systems, Santa Clara, Calif.

[21] Appl. No.: 605,578

[22] Filed: Oct. 30, 1990

[51] Int. Cl.$^5$ .............................................. A61B 17/36
[52] U.S. Cl. .......................................... 606/11; 606/2; 606/15; 250/227.15; 356/73.1
[58] Field of Search ........................... 606/2, 7, 10–16; 128/395–398; 356/73.1, 237; 250/227.15; 350/96.29

[56] References Cited

U.S. PATENT DOCUMENTS

| | | | |
|---|---|---|---|
| 3,863,250 | 1/1975 | McCluskey, Jr. | 340/274 |
| 4,543,477 | 9/1985 | Doi et al. | 250/227.15 |
| 4,812,641 | 3/1989 | Ortiz, Jr. | 250/205 |
| 4,883,054 | 11/1989 | Fuller et al. | 128/395 |

Primary Examiner—Stephen C. Pellegrino
Assistant Examiner—Steven J. Shumaker
Attorney, Agent, or Firm—McCubbrey, Bartels, Meyer & Ward

[57] ABSTRACT

A system and method for detecting breakage in an optical fiber is disclosed. The system includes an acoustic detector coupled to the optical fiber to be monitored for breakage which operates to generate an electrical output signal when the sound of an optical fiber break is detected. A signalling circuit measures the output of the acoustic detector and operates to generate a signal indicative of the output of the acoustic detector, and an indicator circuit is responsive to the output of the signalling circuit to provide an indication of breakage in the optical fiber. In one preferred embodiment, a control circuit is also provided which operates to interrupt light transmission through the optical fiber when breakage of the optical fiber is detected.

11 Claims, 5 Drawing Sheets

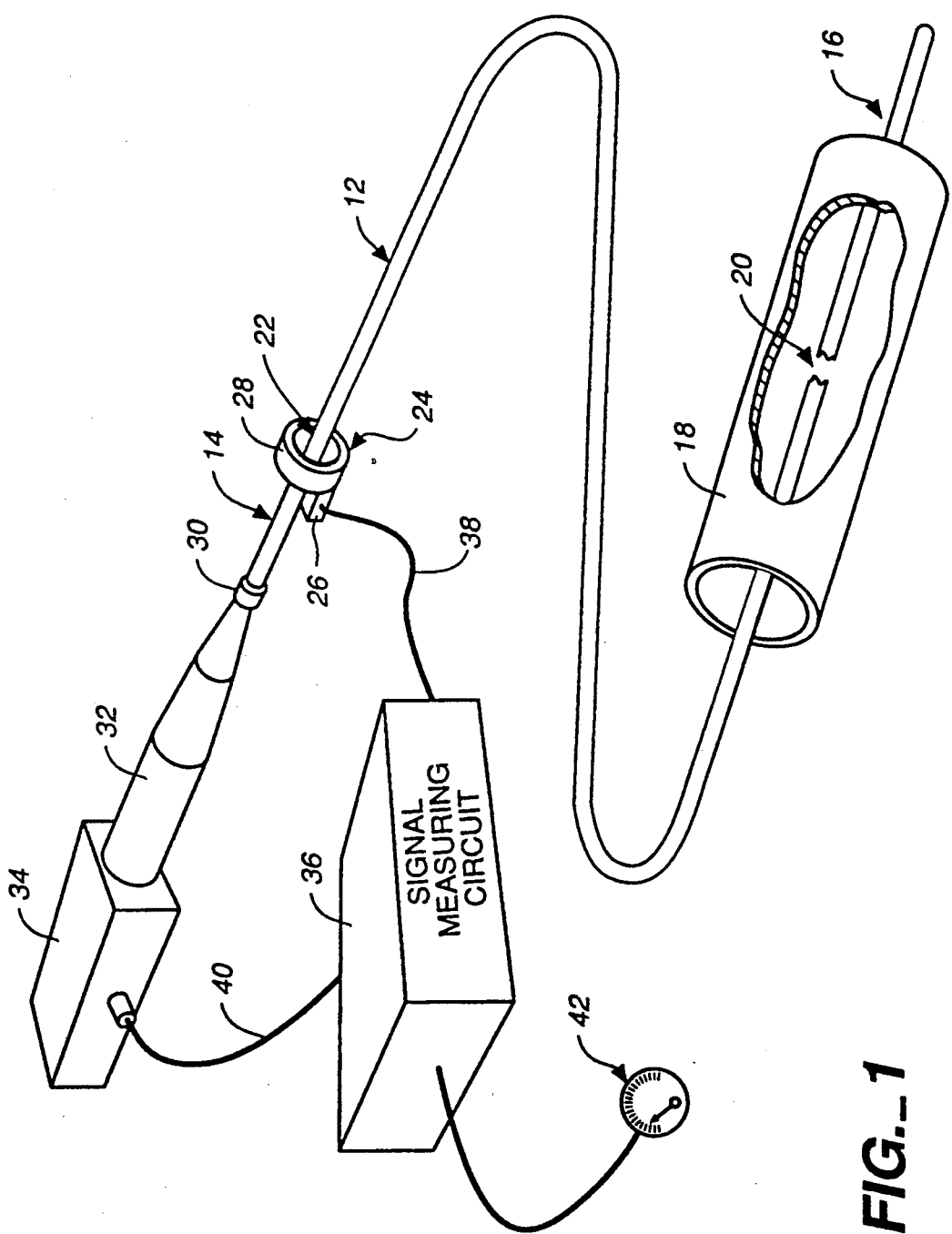
FIG._1

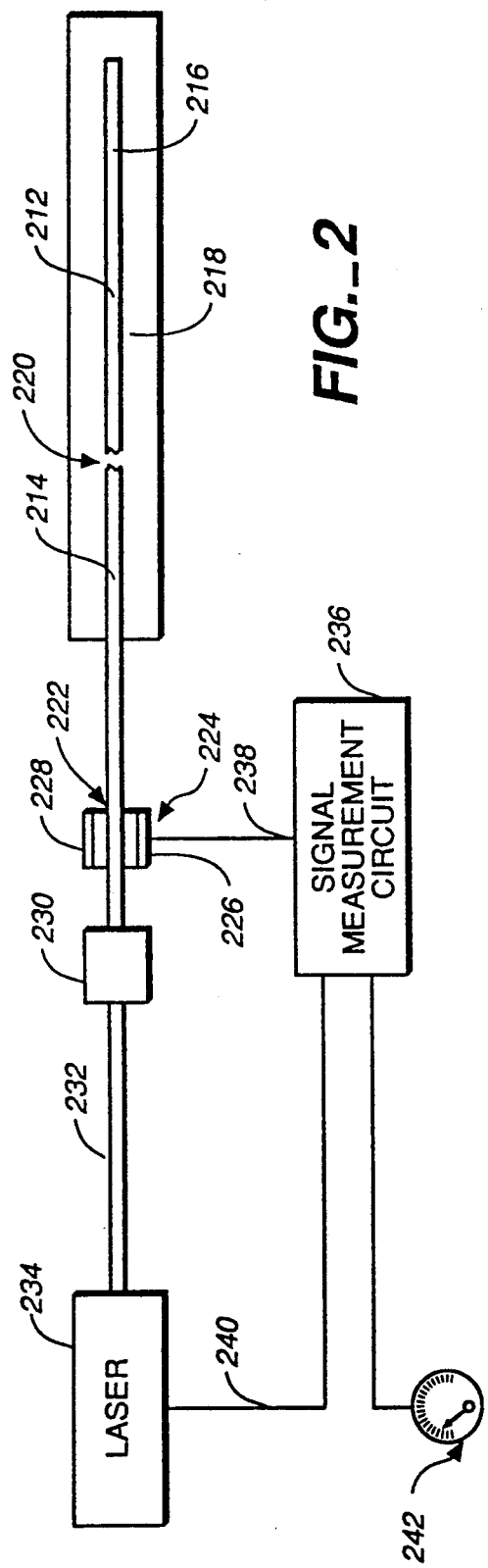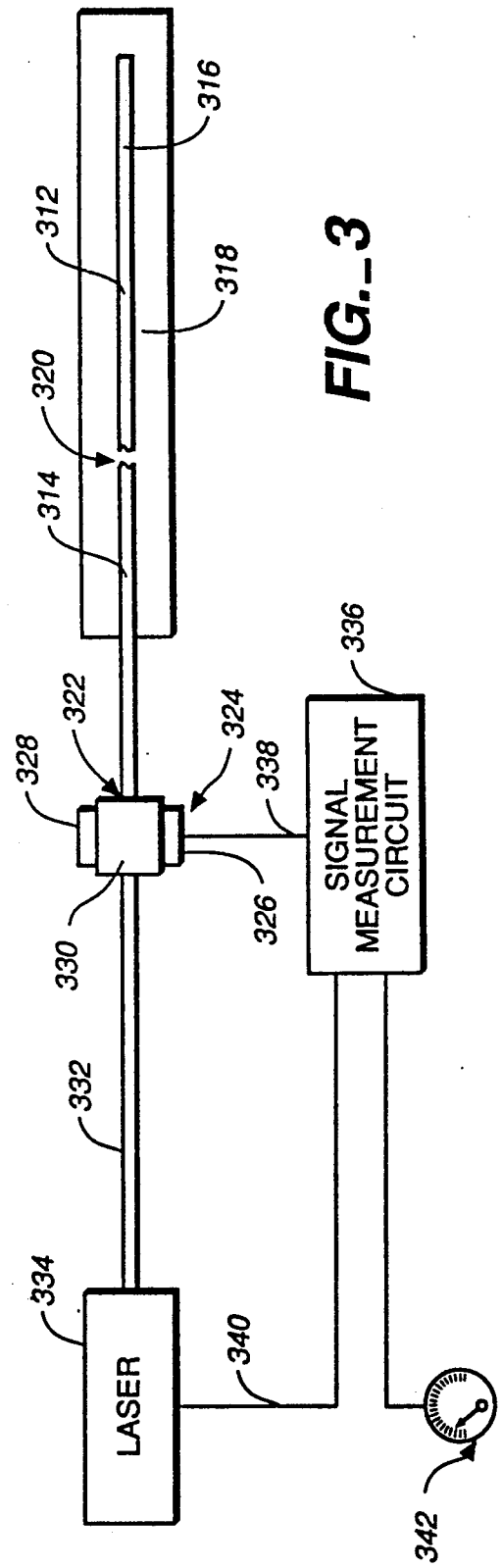

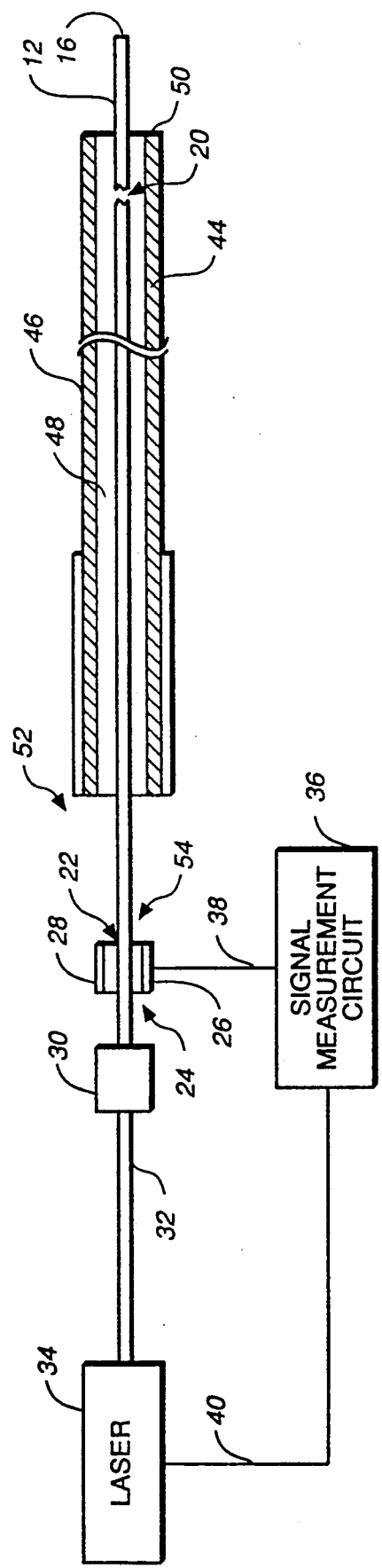
FIG._4

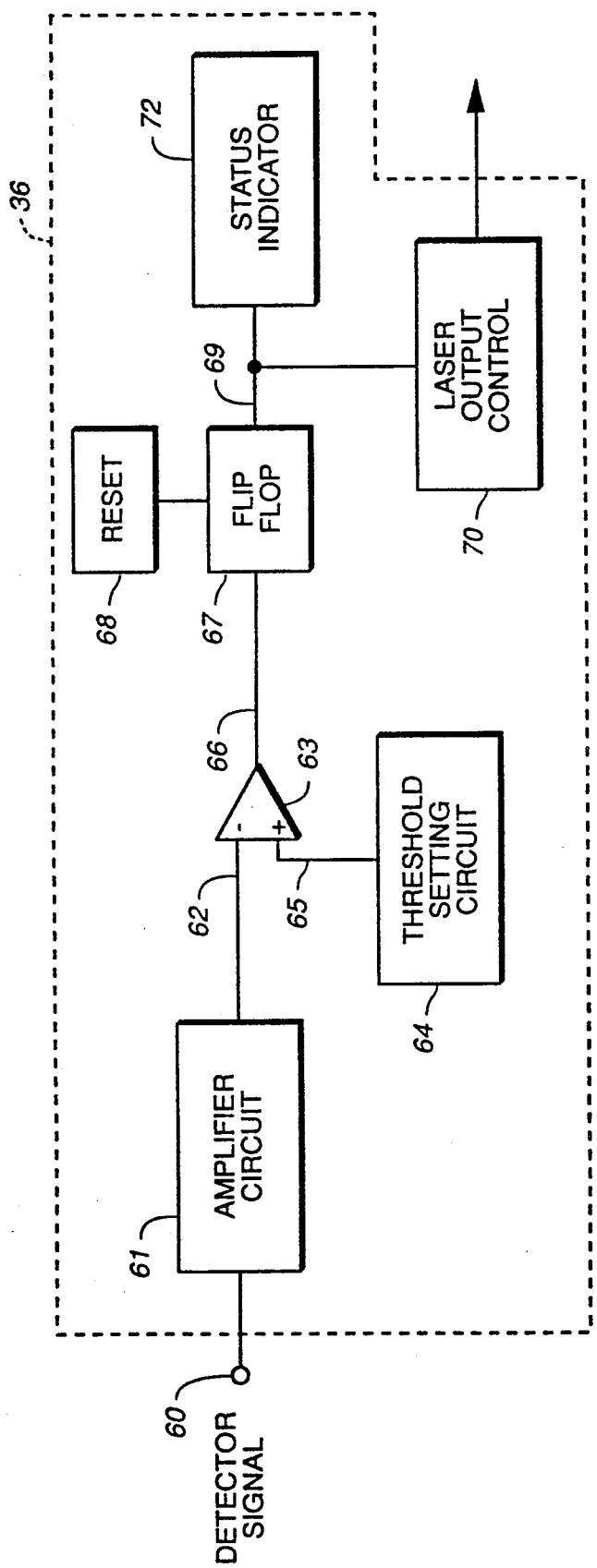
FIG._5
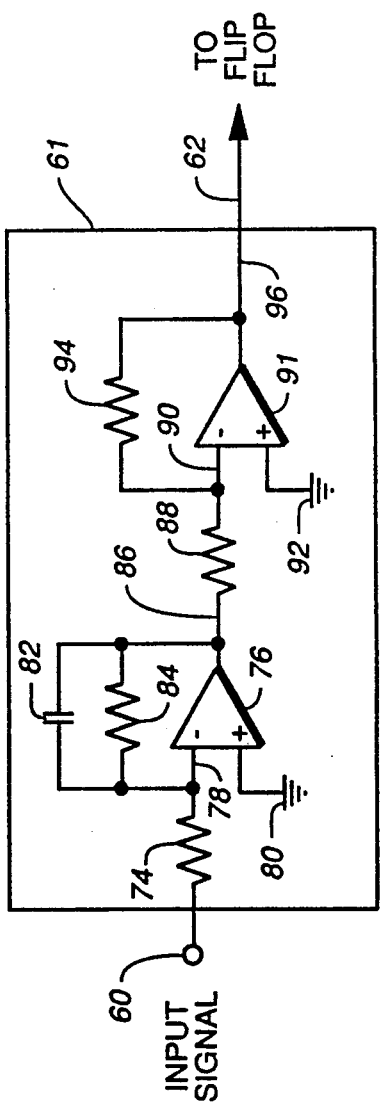
FIG._6

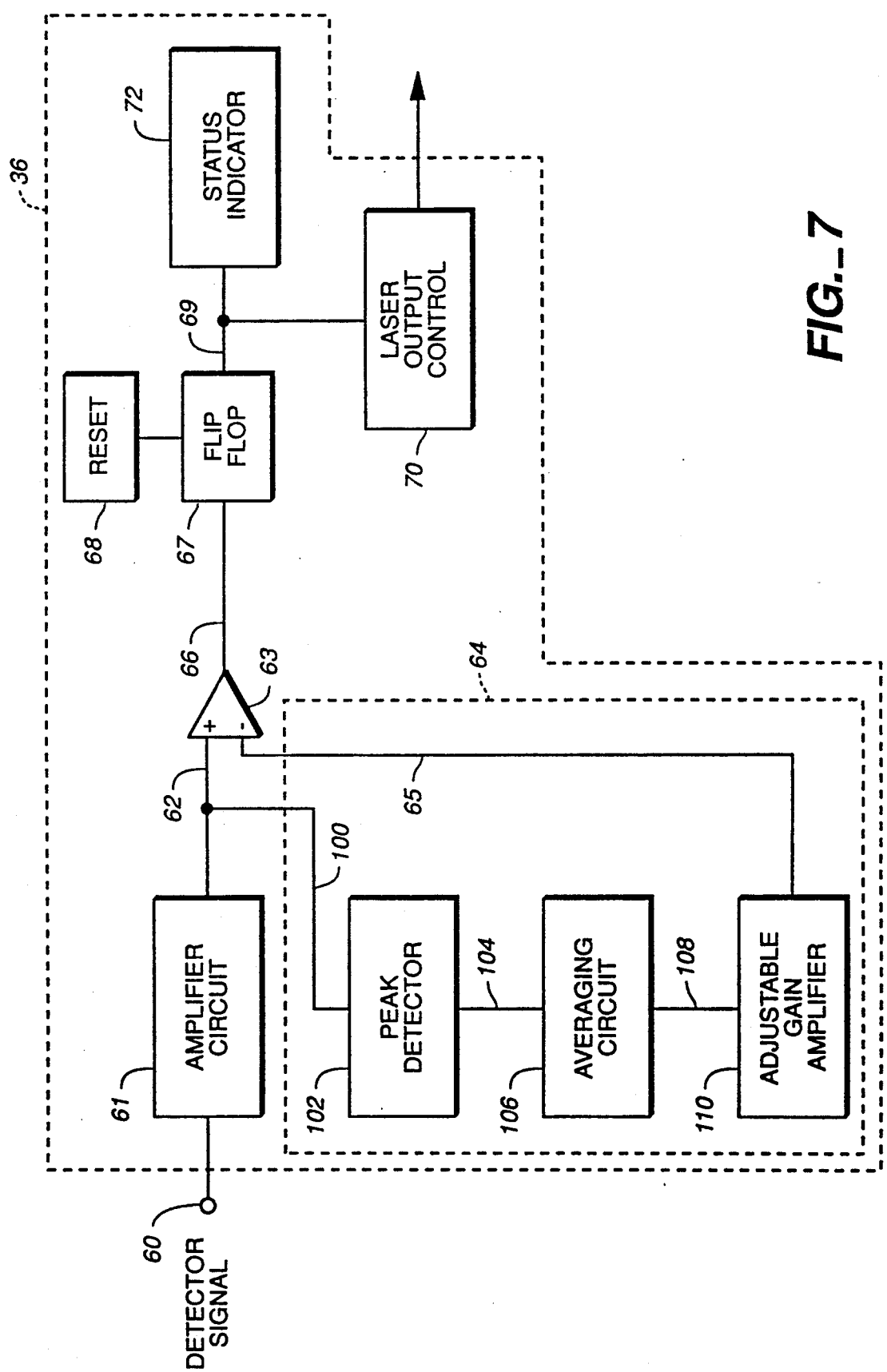
FIG._7

OPTICAL FIBER BREAKAGE DETECTION SYSTEM

FIELD OF THE INVENTION

The present invention relates to the field of optical fibers and more particularly to means of detecting breakage of optical fibers of the type that are used for in vivo medical procedures.

BACKGROUND OF THE INVENTION

The use of optical fibers has become increasingly common in a variety of applications. Optical fibers are particularly useful in the medical arts for apparatus for performing diagnostic and surgical procedures. Lasers and other light sources can used in such applications, but the light must be transmitted into remote body cavities or lumens. The small diameter of optical fibers and their efficient transmission of light provide major benefits in the practicability of such devices.

While the use of optical fibers for these purposes is highly advantageous, there are certain limitations to the use of the fibers that have not thus far been satisfactorily addressed. For example, if the optical fibers are to be used to conduct high energy laser light to a remote location during a surgical procedure, it is important that any break in the light path be detected and the laser light source be immediately interrupted to prevent the escape of light in an uncontrolled manner.

Detection of such a breakage is particularly important in laser angioplasty, in which a catheter containing an optical fiber is inserted into the cardiovascular system and guided to an area of stenosis. After the end of the optical fiber is in place, the laser light emitted from the end of the fiber is directed so as to ablate the stenosis, thereby improving the blood flow through the blood vessel.

The energy transmitted through the fiber is of a sufficient level that if a break in the fiber were to occur and not be detected, significant damage to the vessel and surrounding tissue would occur due to the escape of laser light energy from the break in the fiber. In some circumstances the uncontrolled lasing can endanger nearby personnel.

Furthermore, even if there were no danger from the leakage of light, it would be desirable to detect breakage of the fiber in order to prevent damage to the guiding catheter or surrounding tissue from the broken ends of the fiber.

Also, there are some cases in which light is being transmitted to a remote location by an optical fiber, but there is no simple method of determining that a fiber breakage is the primary cause of the failure in the light to be transmitted along the entire path.

There is at present no available means for detecting such breakage. Prior art glass breakage detection systems assume large panes of glass which shatter upon breakage. Shattering involves large reverberations active over a period of time. These shatter-detectors are responsive to prolonged high frequency signals of high intensity. Optical fibers snap, rather than shatter, and thus produce a very short, impulse-like signal.

Physicians must therefore rely upon the low breakage rate of fibers, and the physicians' personal observation of the progress of the surgery. Hence, there is a need for a reliable means for detecting a breakage in an optical fiber of the type that is utilized to conduct light to a remote location. Furthermore, it would be beneficial if such a breakage detection system would be relatively simple and easily implemented, could provide for the rapid interruption of the light source and would be compatible with a laser angioplasty or surgery apparatus.

Broadly, it is the object of the present invention to provide an improved apparatus and method for the detection of breakage of an optical fiber.

It is a further object of the present invention to provide an apparatus and method for detecting the breakage of an optical fiber which can be used to automatically interrupt the transmission of light through the fiber.

These and other objects of the present invention will be apparent to those skilled in the art from the following detailed description and the accompanying drawings.

SUMMARY OF THE INVENTION

The optical fiber break detection system of the present invention comprises an optical fiber means to be monitored for breakage which has a proximal portion and a distal portion. An acoustic detection means is acoustically coupled to the optical fiber means. A signalling means responds to the output of the acoustic detection means to generate a signal related to the output of the acoustic detection means. This signal is indicative of breakage of the optical fiber. In one preferred embodiment the optical fiber to be monitored extends through an inner channel catheter and is used to transmit laser light through the catheter. The system then further comprises a control circuit to discontinue laser light transmission through the optical fiber when breakage of the optical fiber is detected.

The method of the present invention for detecting breakage of an optical fiber comprises acoustically coupling an acoustic detection means to an optical fiber which is to be monitored for breakage. The acoustic detection means generates an output when sound associated with breakage of the optical fiber is detected. In one preferred embodiment a first signal is generated which is indicative of the output of the acoustic detection means. The first signal is then compared with a reference threshold value, and a second signal is generated when the first signal exceeds that reference threshold value. The second signal is indicative of breakage of the optical fiber.

BRIEF DESCRIPTION OF THE DRAWINGS

FIG. 1 is a perspective view of a general arrangement of a preferred embodiment of the optical fiber break detection system of the present invention.

FIG. 2 is a schematic diagram of a second embodiment of the optical fiber break detection system of the present invention.

FIG. 3 is a schematic diagram of a third embodiment of the optical fiber break detection system of the present invention.

FIG. 4 is a schematic diagram of an optical fiber break detection system similar to that of FIG. 1, disposed in a catheter.

FIG. 5 is a schematic diagram of one embodiment of a signalling circuit 36 suitable for the preferred embodiment illustrated in FIG. 1.

FIG. 6 is a schematic diagram of one embodiment of the sensor amplifier circuit 61 of the signalling circuit 36 of FIG. 5.

FIG. 7 is a schematic diagram of an alternative embodiment of the signalling circuit 36 of the break detection system illustrated in FIG. 1.

DETAILED DESCRIPTION OF THE PREFERRED EMBODIMENT

As is shown in the drawings, which are provided for purposes of illustration and not by way of limitation, the invention is embodied in an optical fiber break detection system which includes an acoustic detector coupled to an optical fiber to be monitored for breakage. The acoustic detector operates to generate an electrical output signal responsive to sound associated with the breakage of an optical fiber.

It has been discovered that the intensity of the sound of fracture of an optical fiber is many times greater than that of any other sound typically generated in or near an optical fiber during most known uses. In particular, this is true in medical applications of optical fibers. Thus, the detection of optical fiber breakage is easily accomplished using the apparatus described herein.

In the presently preferred embodiment, a signalling circuit receives the output signal from the acoustic detector, and generates a signal indicative of the output of the acoustic detector. An indicator circuit is also provided which responds to the output of the signalling circuit to provide an indication of breakage in the optical fiber. In the embodiment shown in FIG. 4, the optical fiber extends through an inner channel of an angioplasty catheter to transmit laser light through the catheter. A control circuit is provided which is responsive to the output of the signalling circuit and operates to discontinue laser light transmission through the optical fiber when breakage of the optical fiber is detected.

As is illustrated in FIG. 1, the currently preferred embodiment of the invention includes an optical fiber 12 to be monitored having a fiber proximal portion 14 and a fiber distal portion 16. A housing or other structural apparatus 18 surrounds or is otherwise associated with a fracture 20 in the fiber 12. Fracture 20 can be located between the fiber proximal portion 14 and the fiber distal portion 16, inclusive. The detector 24 includes an acoustic transducer 26 which is preferably a piezoelectric transducer held in contact with the fiber proximal portion 14 of optical fiber 12 by clamp 28, thereby assuring acoustic communication between transducer 26 and optical fiber 12. Alternatively, transducer 26 may be adhesively bonded to optical fiber 12 by any suitable adhesion which may provide acoustic communication between the fiber and the transducer.

The breakage sound in an optical fiber is essentially an impulse. True impulses have uniformly broad spectra containing significant power at every frequency. Therefore the breakage impulse should contain a signal at the resonant, otherwise known as natural, frequency of acoustic detector 24, regardless of the particular natural frequency of any given acoustic detector Therefore acoustic detector 24 will respond to the breakage impulse by resonating at the acoustic detector 24's natural frequency and producing an electronic signal which is the acoustic detector 24's impulse response. Experiments have demonstrated no difficulty in obtaining resonance for acoustic detectors with natural frequencies of roughly 200 kHz and 600 kHz.

The output of transducer 26 may be conducted by an electrical conductor or wire 38 to a signaling circuit 36 which detects the distinctive signal associated with breakage of the optical fiber 12. The signalling circuit 36 also preferably generates an output signal which provides an indication of such breakage. This output signal is input to a status indicator display or meter 42. Optical fiber 12 may be connected to a light source 34 and connecting optical light conducting apparatus 32 by optical connector 30. In one preferred embodiment, the output of signalling circuit 36 may be used to interrupt the output of light source 34 by control line 40.

FIG. 2 illustrates an alternative embodiment of the optical fiber break detection system of the present invention. The system is used with optical fibers embedded in or adhesively bonded to an otherwise relatively inaccessible medium or substrate 218 such as a building, pipeline, roadway, or aircraft structure. The optical fibers may also be combined during building construction into a matrix on the surface of areas to be monitored for security, such as floors, bank vaults, or walls to thereby detect disturbances or breakages in the surrounding or underlying substrate 218. An optical fiber break detection system with an array of optical fibers could also be arranged within the wrapping of packages or parcels to monitor whether the package has been tampered with in transit. Thus, fracture 220 in an optical fiber can be detected in a relatively accessible proximal area 222 outside the medium or substrate, by an acoustic detector 224 acoustically coupled to the optical fiber.

While a currently preferred acoustic detector is a piezoelectric transducer 226, of conventional piezoelectric ceramic material, coupled to the optical fiber by a clamp 228, the transducer 226 may be adhesively bonded to the optical fiber 212 by the use of an appropriate adhesive.

The electrical output of the piezoelectric transducer may be transmitted along wires 238 to a signalling circuit 236, which also typically includes an indicator circuit which indicates whether breakage of the optical fiber has been detected. When laser light is transmitted through optical fiber 212, the output of signalling circuit 236 may be communicated through a control line such as electrical conductor 240 to laser 234. This signal may be used to instruct laser 324 to interrupt the light path between the laser 234 and optical fiber 212 and to thereby discontinue transmission of the laser light. Alternatively, the indication of fiber breakage may be displayed on a display 242, which can be a meter or similar device.

FIG. 3 illustrates a system similar to that of FIG. 2. Here optical fiber 312 is connected to an optical light conducting apparatus such as a source optical fiber 332 and a light source such as a laser and related optics 334 by a fiber optic connector 330. Thus piezoelectric transducer 326 may also be clamped, or otherwise acoustically coupled to the fiber optic connector 330, which would in turn transmit sound waves from the optical fiber to the acoustic detector.

The preferred embodiment of the present invention is best understood in light of FIG. 4, which is a schematic diagram of one alternative embodiment of the preferred embodiment of FIG. 1. As described above, the optical fiber break detection system includes an optical fiber 12 having a fiber proximal portion 32 and a fiber distal portion 16. Optical fiber 12 is placed within an elongated catheter tubular member 44, which corresponds to structural apparatus 18 of FIG. 1. One such implementation of elongated catheter tubular member 44 may be an angioplasty catheter adapted as a laser catheter. An optical fiber within such a catheter would be quite inaccessible to monitoring for breakage of the optical fiber during normal angioplasty procedures.

FIG. 4 shows a typical laser catheter, including an outer catheter wall 46, and at least one inner catheter lumen 48, with a catheter distal end 50 and a catheter proximal end 52. A break 20 in an optical fiber 12 can be detected in a relatively accessible fiber proximal area 54 outside of the catheter, by an acoustic detector 24 acoustically coupled to the optical fiber. As previously discussed, the piezoelectric transducer 26 may be coupled to optical fiber 12 by a clamp 28, although those skilled in the art will recognize that a variety of means may be used to acoustically couple transducer 26 to optical fiber 12, and that transducer 26 may be coupled to optical fiber 12 in a variety of locations.

The output signal of transducer 26 is transmitted along conductor 38 to the signalling circuit 36, to indicate whether breakage of the optical fiber has been detected. Since the escape of laser energy through a break in optical fiber 12 during a laser procedure within the body could have serious consequences, it is preferred in this embodiment to terminate transmission of the laser light upon detection of breakage. The output signal of signalling circuit 36 is communicated through an electrical connection 40 to control the output of laser 34, to thereby rapidly disengage the output of laser 34 and thereby prevent potential trauma to a patient.

One embodiment of the acoustic detector signalling circuitry of the invention is schematically illustrated in FIG. 5. The electrical output signal of a piezoelectric transducer is received at the acoustic detector signal input 60, and is amplified in the acoustic detector amplifier circuit 61. The amplified signal is communicated via output line 62 to a threshold analog comparator 63. Threshold setting circuit 64 produces a signal at voltage output 65, which is compared by comparator 63 with the output signal on output line 62 from acoustic detector amplifier circuit 61.

The output signal on line 66 from analog comparator 63 is directed to a flip-flop circuit 67. Flip-flop circuit 67 is triggered to generate an output signal indicative of a change in logic state when the threshold signal level is exceeded. Since the output of flip-flop 67 can be utilized in one embodiment to discontinue laser light transmission, a manual reset 68 is also provided. This allows resumption of laser operation if optical fiber 12 is either replaced or repaired. The logic state output is communicated via output line 69 of flip-flop 67 to a laser output control circuit 70, and to a status indicator 72. Status indicator 72 may be implemented as an LED, or a similar device.

The operation of the acoustic signalling circuitry illustrated in FIG. 5 will now be described in greater detail. The amplified signal from acoustic detector amplifier circuit 61 is applied to the inverting input of analog comparator 63 through line 62. Similarly, output of threshold setting circuit 64 is applied to the non-inverting input of analog comparator 63 through line 65. If the voltage from acoustic detector amplifier circuit 61 exceeds the voltage from threshold setting circuit 64, the output signal from analog comparator 63 changes state. This will occur if there is a fracture of optical fiber 12. If flip-flop 67 is in a reset state, the state change of signal 66 will cause the output of flip-flop 67 to change state also.

Status indicator 72 is sensitive to the change in state present on output line 69 of flip-flop 67, so that an indicator light or meter will be activated to indicate that a fracture of the optical fiber has occurred. Alternatively, other display circuits, such as a liquid crystal display, or acoustical alarms, could also be utilized in the indicator circuit to provide an effective warning to an operator that breakage of the optical fiber had occurred.

At the same time, the laser output control circuit 70 is sensitive to the state change of the output of flip-flop 67. Upon detecting the change, laser output control circuit 70 signals to laser 34 to turn off laser output power. Manual reset 68 allows flip-flop 67 to be reset once the broken optical fiber is repaired or replaced.

FIG. 6 shows an embodiment of the acoustic detector amplifier circuit 61 in more detail. The electrical output signal of piezoelectric transducer 26 of FIGS. 1 and 4 is received at acoustic detector signal input 60 of acoustic detector amplifier circuit 61. Acoustic detector signal input 60 is connected through a resistor 74 to the inverting input 78 of a first operational amplifier 76. The non-inverting input of first operational amplifier 76 is connected to ground 80. Also connected in parallel between the inverting input of first operational amplifier 76 and first operational amplifier output 86 is a capacitor 82 and a resistor 84. Resistor 84 is preferably a potentiometer, to allow adjustment of the sensitivity of the amplifier circuit to signals which would be detected by the piezoelectric acoustic transducer 26.

First operational amplifier output 86 of first operational amplifier 76 is connected through resistor 88 to the inverting input 90 of a second operational amplifier 91. The non-inverting input of second operational amplifier 91 is connected to ground 92. A resistor 94 is connected between the inverting input 90 of second operational amplifier 91 and second operational amplifier output 96, which is connected in turn by line 96 to acoustic detector amplifier circuit output 61.

An alternative embodiment of the acoustic signalling circuitry is illustrated in FIG. 7. The circuit of FIG. 7 is similar in function to that of FIG. 5, except that threshold setting circuit 64 can produce an adjustable, adaptive threshold voltage output. An electrical line 100 connects output line 62 of acoustic detector amplifier circuit 61 to a peak detector circuit 102. Peak detector circuit 102 detects the peak background noise level from the acoustic detector amplifier circuit 61 and provides a peak noise signal level via line 104 to an averaging circuit 106. detector amplifier circuit 61 and provides a peak noise signal level via line 104 to an averaging circuit 106.

Averaging circuit 106 determines an average signal level over a predetermined period of time, and generates an averaged noise level signal. This averaged noise level signal can be directly input to analog comparator 63 as a threshold voltage signal 65. The averaged noise level signal is also preferably output via line 108 to an adjustable gain amplifier 110. The gain of the averaged noise level signal may thus be manually set to produce a slowly changing voltage output 65 related to average acoustic and system noise derived from detector amplifier signal output 62. The threshold can thus be adaptive to changes in noise levels in different environments and applications of the optical fiber breakage detection system, and the sensitivity of the system can be further finely adjusted by an operator.

From the foregoing, it will be appreciated that the present invention provides an easily implemented method and apparatus for the detection of breakage of an optical fiber. The present invention requires access to only one end of the fiber, and requires minimal power for the indicator circuitry. The method and system of the present invention can provide a rapid interruption of transmission of light in the event of breakage, which is of particular benefit in a laser catheter apparatus.

While several preferred and alternative embodiments of the invention have been herein described, it will be obvious to those skilled in the art that it is susceptible to numerous modifications and embodiments. Accordingly, the present invention is to be limited solely by the scope of the following claims.

What is claimed is:

1. An optical fiber breakage detection system comprising:

optical fiber mean to be monitored for breakage, said optical fiber means having a proximal portion and a distal portion;

acoustic detection means for generating an output electrical signal in response to acoustic energy having a value representing a level of said acoustic energy, said acoustic detection means being substantially acoustically coupled to said optical fiber means; and siganlling means electrically connected to said acoustic detection means and responsive to said output electrical signal of said acoustic detection means for comparing said output electrical signal to a predetermined reference threshold and for generate a first electrical signal when the value of said output electrical signal exceeds said .reference threshold, the generation of said first electrical signal being indicative of breakage of said optical fiber means.

2. The system of claim 1, wherein:

said optical fiber means extends through a lumen of a catheter; and said optical fiber means is operatively coupled to a source of light for receiving light therefrom to be transmitted through said optical fiber means.

3. The system of claim 2, wherein said system further comprises control means electrically connected to said signalling means and responsive to said first electrical signal, said control means generating a control signal which is operative upon said source of light to cause said source of light to interrupt transmission of light through said optical fiber means when breakage of said optical fiber means is indicated by said first electrical signal.

4. The system of claim 3, wherein said source of light is a laser.

5. The system of claim 1, wherein said signalling means further comprises:

averaging means for determining an average value represented by said output electrical signal of said acoustic detection means over time; and comparison means for comparing an instantaneous value represented by said output electrical signal of said acoustic detection means with said average value represented by said output electrical signal, said comparison means generating a comparison signal when said instantaneous value of said output electrical signal from said acoustic detection means exceeds said average value of said output electrical signal.

6. The system of claim 1, wherein said signalling means further comprises means for adjusting said reference threshold.

7. The system of claim 1, wherein said acoustic detection means comprises means for converting sound waves into electrical signals.

8. The system of claim 1, wherein said acoustic detection means comprises a piezoelectric transducer.

9. A method for detecting breakage of an optical fiber, comprising the steps of:

substantially acoustically coupling acoustic detection means for detecting acoustic energy to an optical fiber which is to be monitored for breakage, said acoustic detection means being operative to generate an output electrical signal representating a level of said acoustic energy is detected; and electrically connecting said acoustic detection means to a signalling means which compares said output electrical signal to a predetermined reference threshold and generates a first electrical signal when the value of said output electrical signal exceeds said reference threshold, generation of said first electrical signal being indicative of breakage of said optical fiber.

10. The method of claim 9, wherein said optical fiber is operatively connected to a source of light to be transmitted through said optical fiber, and further comprising the step of generating a control signal for interrupting transmission of the light through said optical fiber means, said control signal being responsive to said first electrical signal.

11. The method of claim 9, wherein reference threshold value is determined from a function over time of the instantaneous value of said output signal from said acoustic detection means.

* * * * *